(12) United States Patent
Raju et al.

(10) Patent No.: US 8,149,004 B2
(45) Date of Patent: Apr. 3, 2012

(54) CORROSION SENSOR FOR MONITORING AND CONTROLLING LUBRICANT ACIDITY

(75) Inventors: Raghurama A. Raju, Bangalore (IN);
Sanjeeb Tripathy, Bangalore (IN);
Jicang Zhou, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 435 days.

(21) Appl. No.: 11/655,271

(22) Filed: Jan. 19, 2007

(65) Prior Publication Data

US 2008/0174323 A1 Jul. 24, 2008

(51) Int. Cl.
*G01R 27/08* (2006.01)
*G01N 17/00* (2006.01)

(52) U.S. Cl. ............. 324/700; 324/698; 324/721; 73/86
(58) Field of Classification Search .................. 324/698, 324/700, 721; 73/86
See application file for complete search history.

(56) References Cited

U.S. PATENT DOCUMENTS

| | | | | |
|---|---|---|---|---|
| 3,155,934 A * | 11/1964 | Messick et al. | ................ | 338/13 |
| 4,338,563 A * | 7/1982 | Rhoades et al. | ............. | 324/700 |
| 4,675,662 A * | 6/1987 | Kondo et al. | ................ | 340/631 |
| 4,792,791 A * | 12/1988 | Cipris et al. | .................. | 340/603 |
| 4,840,719 A | 6/1989 | Jasinski | | |
| 4,863,572 A | 9/1989 | Jasinski | | |
| 5,089,780 A | 2/1992 | Megerle | | |
| 5,274,335 A | 12/1993 | Wang et al. | | |
| 5,332,961 A | 7/1994 | Hammerle | | |
| 5,674,401 A * | 10/1997 | Dickert et al. | ................ | 210/695 |
| 5,777,210 A | 7/1998 | Voelker et al. | | |
| 6,091,484 A | 7/2000 | Venica et al. | | |
| 6,131,443 A * | 10/2000 | Duncan | ............................. | 73/86 |
| 6,223,589 B1 * | 5/2001 | Dickert et al. | ............... | 73/61.45 |
| 6,286,363 B1 | 9/2001 | Discenzo | | |
| 6,705,242 B2 * | 3/2004 | Donovan | ...................... | 110/341 |
| 6,801,857 B2 | 10/2004 | Despax et al. | | |
| 7,043,402 B2 * | 5/2006 | Phillips et al. | ................ | 702/184 |
| 2002/0011095 A1 | 1/2002 | Park et al. | | |
| 2002/0196439 A1 | 12/2002 | Engler et al. | | |
| 2003/0046985 A1 | 3/2003 | Schoess | | |
| 2003/0179002 A1 | 9/2003 | Beylich et al. | | |
| 2003/0196479 A1 | 10/2003 | Kasen et al. | | |
| 2004/0035398 A1 | 2/2004 | Klugl et al. | | |
| 2007/0074563 A1 | 4/2007 | Liu et al. | | |

FOREIGN PATENT DOCUMENTS

| | | |
|---|---|---|
| EP | 0980522 | 2/2000 |
| EP | 1004872 | 5/2000 |
| EP | 1466170 | 10/2004 |
| GB | 2345342 | 7/2000 |
| GB | 2384312 | 7/2003 |
| JP | 57098842 | 6/1982 |
| JP | 57098849 | 6/1982 |
| JP | 11257042 | 9/1999 |
| WO | WO-0043773 | 7/2000 |
| WO | WO-0050894 | 8/2000 |
| WO | WO-03038394 | 5/2003 |
| WO | WO-2004065957 | 8/2004 |

* cited by examiner

*Primary Examiner* — Melissa Koval
*Assistant Examiner* — Farhana Hoque
(74) *Attorney, Agent, or Firm* — Schwegman, Lundberg, & Woessner P.A.

(57) ABSTRACT

A corrosion sensor having a corrodible element that is corrodible in a lubricant or hydraulic oil, wherein the corrosion sensor is adapted to monitor degradation of the lubricant or hydraulic oil is disclosed.

29 Claims, 4 Drawing Sheets

CORROSION SENSOR FOR MONITORING AND CONTROLLING LUBRICANT ACIDITY

RELATED APPLICATIONS

None.

FIELD OF INVENTION

The embodiments of the invention relate to a corrosion sensor and method to monitor the acidity of a lubrication (lube) oil and hydraulic oil.

BACKGROUND

Motor oil is a type of liquid oil used for lubrication by various kinds of internal combustion engines. Other benefits from using motor oil include cooling by carrying heat away from moving engine parts and often include cleaning and corrosion inhibition in internal combustion engines. Motor oil is used as a lubricant in various kinds of internal combustion engines in which there are contacting parts which move against each other at high speeds, often for prolonged periods of time. Hydraulic oils are used for automotive and other braking systems. Such rubbing motion causes friction, absorbing otherwise useful power produced by the motor and converting the energy to useless heat. Lubricating and hydraulic oils makes a film between surfaces of parts moving against each other so as to minimize direct contact between them decreasing friction, wear, and production of excessive heat. Coating metal parts with oil also keeps them from being exposed to oxygen, which inhibits their oxidation at elevated operating temperatures. In summary, in ideal situation, a lubricant will physically separate these asperities with an oil film. This is called full fluid film lubrication. When the proper lubricant is used and the proper load is applied, the asperities are not in contact and no wear occurs.

Most motor oils are made from a heavier, thicker petroleum hydrocarbon base stock derived from crude oil, with additives added as needed to improve the properties. Among various oil additives, anti-oxidants, the viscosity index improvers, detergents and dispersants are the most important to help keep the engine clean by minimizing sludge buildup, corrosion inhibitors, and alkaline additives to neutralize acidic oxidation products of the oil. For examples, a certain amount of anti-oxidants is usually charged to the base oil in order to stabilize the base oils or other additives from degradation via oxidation. Commercial oils also have additives like detergents and dispersants, the former is to neutralize the acids in oils generated during service while the later is to stabilize the particulates in oils from depositing onto the surface. Moreover, most commercial oils have a minimal amount of zinc dialkyldithiophosphate as an anti-wear additive to protect contacting metal surfaces with zinc and other compounds in case of metal to metal contact. The quantity of zinc dialkyldithiophosphate is limited to minimize adverse effect on catalytic converters.

There are also other additives available commercially which can be added to the oil by the user for purported additional benefit. Some of these additives include: Zinc dialkyldithiophosphate (ZDDP) additives, which typically also contain calcium, are available to consumers for additional protection under extreme-pressure conditions or in heavy duty performance situations. ZDDP and calcium additives are also added to protect motor oil from oxidative breakdown and to prevent the formation of sludge and varnish deposits.

During services in engines, there is inevitably some exposure of the oils to products of internal combustion, and microscopic coke particles from black soot accumulate in the oil during operation. Also, since no solid surface is perfectly smooth, opposing friction surfaces have peaks called asperities that come in contact with each other. As is known, rubbing of metal engine parts inevitably produces some microscopic metallic particles from the wearing of the surfaces. Such particles could circulate in the oil and grind against the part surfaces causing erosion and wear. The oil filter removes many of the particles, but eventually the oil filter gets filled up. Moreover, the motor oil and especially the additives also undergo oxygen, thermal and mechanical degradation. For these reasons, the oil quality in engine will continuously deteriorate till it no longer functions well as a lubricant and, therefore, the oil and the oil filter need to be periodically replaced.

The vehicle manufacturer specifies which grade of oil should be used for the vehicles it produces. The manufacturer also specifies how often the oil changes should be made. For example, most people in the United States believe that a common oil change frequency should be every 3000 miles or every 3 months, whichever comes sooner. This 3000 mile oil change interval has been relentlessly promoted by oil changing companies for decades. It had a scientific basis when engines used non-multi-weight, non-detergent oil. It no longer has any scientific basis, but it is still being promoted by certain entities, most notably the oil change industry in the United States (including car dealerships). Indeed, studies have shown more wear occurs with fresher (1000-2000 mile) oil. This is attributed to additives re-establishing themselves, TBN converging, and filters becoming more efficient. Most manufacturers recommend oil change intervals of 6,000 miles or more for modern cars and heavy duty trucks. In Europe, by contrast, where the influence of oil companies has been much less, oil is typically changed only at a major service interval, between 10,000 and 15,000 miles for a modern car and heavy duty truck. For convenience, the oil filter is usually also replaced at the time the oil is changed.

All the above mentioned used oil replacement mechanism are approaches based on empirical correlation derived from correlation between oil properties analysis results and engine performance test. A number of oil analysis experiments are now carried out in oil analysis labs, examples of which are described below.

First, to maintain a lubricating film between moving parts, the viscosity of oils must be high enough, but low enough that the oil can flow around the engine parts satisfactorily to keep them well coated under all conditions. The Viscosity Index is a measure of how much the oil's viscosity changes as temperature changes. A higher viscosity index indicates the 'viscosity' changes less with temperature than a lower viscosity index.

Second, another test done on oil is to determine the Total Base Number (TBN), which is a measurement of the reserve alkalinity of an oil to neutralize acids. The resulting quantity is determined as mg KOH/(gram of lubricant). Analogously, Total Acid Number (TAN) is the measure of a lubricant's acidity.

Finally, still other tests include zinc, phosphorus, or sulfur content, and testing for excessive foaming. Among the various oil analysis, it is recommended that oil viscosity, oil acidity (total acidity number, TAN, or total base number, TBN), particulates in oils and oil oxidation onset time, etc., are most important parameters for oil quality monitoring purpose.

In the prior art of oil quality measurements, "external oil analysis" is the most common mode. This means that one need to get some oil samples from engines and send it to oil analysis labs for measurement. This non real-time measurement of oil quality has several disadvantages and is typically regarded as a "protective approach" for engine maintenance. Recently, it is highly recommended to take the "proactive approach" of engine maintenance based on real time oil quality monitoring. This invention aims to provide a real-time approach for oil acidity (TAN & TBN) measurement for the purpose of "proactive" engine maintenance.

SUMMARY OF THE INVENTION

The embodiments of this invention relate to a corrosion sensor comprising a corrodible element that is corrodible in a lubricant, wherein the corrosion sensor is adapted to monitor degradation of the lubricant. Preferably, the corrosion sensor is adapted to be placed in a lubricant bath containing the lubricant. Preferably, the corrodible element comprises a metal plate, metal foil, metal wire, or a metal alloy plate, metal alloy foil, metal alloy wire, or a metal oxide plate, metal oxide film or metal oxide wire. Preferably, the metal foil or wires comprise a material selected from the group consisting of K, Na, Ba, Mg, Al, Zn, Fe, Ni, Sn, Pb, Cu, Ag, their alloy, or metal oxides of the above metals individually or a combination of two or more elements as compounds. Preferably, the wires have a thickness/diameter in a range of about 1 nanometer to 1 mm. Preferably, the corrosion sensor further comprises a vacuum airlock chamber or a small hermetically sealed non-metallic enclosure comprising a reference corrodible, wherein corrosion of the reference corrodible element is substantially zero.

Another embodiment of the invention relates to a corrosion sensor system comprising (a) a corrosion sensor comprising a corrodible element, wherein the corrosion sensor in-situ monitors acidity of a lubricant, and (b) an electronic module connected to the corrosion sensor for monitoring and storing data to allow for analysis of corrosion of the corrodible element. Preferably, the corrodible element comprises Cu. Preferably, the corrosion sensor comprises a vacuum airlock chamber or a small hermetically sealed non-metallic enclosure comprising a reference corrodible element, wherein corrosion of the reference corrodible element is substantially zero and is provided for automatic temperature compensation of the corrodible element by neutralizing a change of resistance of the corrodible element that occurs due to variations that impact both the corrodible element and the reference corrodible element. The corrosion sensor system could further comprise a reference corrosion sensor comprising a sealed corrodible element that is permanently sealed in a hermetically sealed non-metallic enclosure wherein corrosion of the sealed corrodible element is substantially zero, and further wherein the electronic module is adapted to compare an amount of corrosion of the corrodible element versus that of the sealed corrodible element.

As will be realized, this invention is capable of other and different embodiments, and its details are capable of modifications in various obvious respects, all without departing from this invention. Accordingly, the drawings and description are to be regarded as illustrative in nature and not as restrictive.

DETAILED DESCRIPTION

Figure 1:
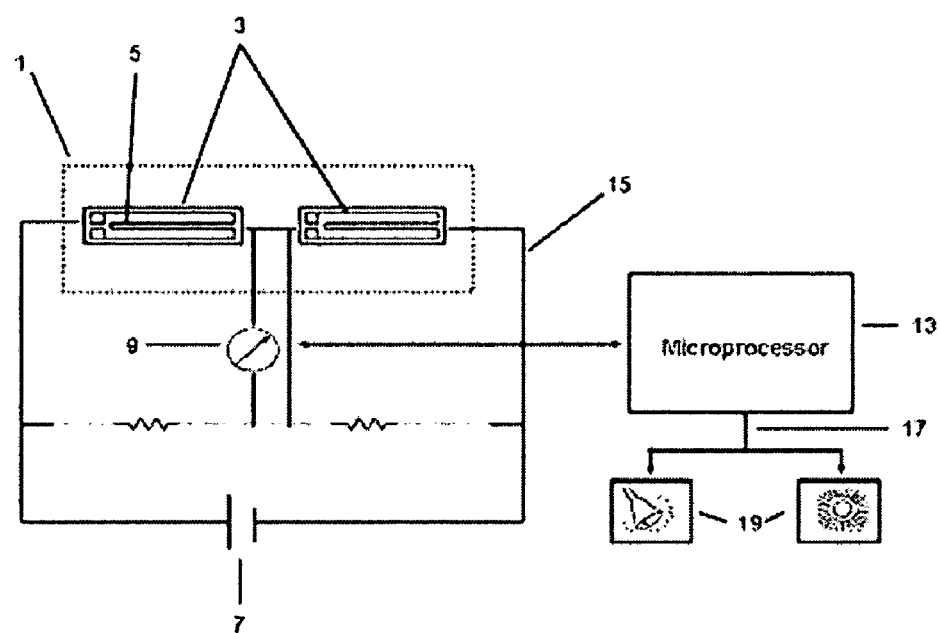
FIG. 1 shows the schematic diagram of an embodiment of a device for monitoring the acidity of a lubricant or hydraulic oil.

As used in the specification and claims, the singular forms "a", "an" and "the" include plural references unless the context clearly dictates otherwise.

The term "in-situ" refers to in the original or natural place or site. The term "to monitor in-situ" means to monitor a thing while leaving the thing in the original place or position and without substantially altering the position of the thing from its original position.

The term "lubricant" refers to any substance, such as grease or oil, which reduces friction when applied as a surface coating to moving parts.

The term "degradation" in the context of a lubricant refers to a decomposition of a compound, optionally exhibiting intermediate products during degradation.

The term "acidity" refers to a property of being an acid. An "acid" is a proton donor and a "base" is a proton acceptor. The acid is said to be dissociated after the proton is donated. An acid and the corresponding base are referred to as conjugate acid-base pairs. This definition includes water-insoluble substances.

The term "corrosion" refers to a chemical (often electrochemical) process that destroys a material. Typically it refers to corrosion of metals, but any other material (e.g., plastic or semiconductor) will also corrode. The simplest example of metallic corrosion is the rusting of iron in air. Iron is spontaneously oxidized by the oxygen in air to iron oxides (while the oxygen is being reduced). Metallic corrosion is very often an electrochemical process. It is electrochemical when the metal is immersed in a solution, but even in atmospheric corrosion a thin film of condensed moisture often covers the surface. The metal in the corrosive solution essentially acts as a short-circuited electronic cell. Different areas of the surface act as anode and cathode, at the anodic areas the metal is oxidized to an oxide while at the cathodic areas the dissolved oxygen is being reduced. The spontaneous complementary oxidation/reduction processes of "rusting" are spatially separated while an electrical current is flowing "internally" from one part of the corroding metal to another; the current is totally "wasted" as it produces no useful work but only generates heat. (A cell arrangement like this is often called a "local cell.") Corrosion products are typically oxides, but other products (e.g., sulfides) can also form depending on the environment. Corrosion involves oxidation of the corroding material in the general sense of the term.

The term "corrodible" refers to a property of a material that can undergo corrosion.

An "electrochemical series" is a tabulation on which various substances, such as metals or elements, are listed according to their chemical reactivity or standard electrode potential. It is usually ordered with increasing standard electrode potentials (most negative on top). For metals, the order indicates the tendency to spontaneously reduce the ions of any other metal below it in the series. During electrolytic (i.e., a process that decomposes a chemical compound into its elements or produces a new compound by the action of an electrical current) reduction of cations (i.e., positively charged ions, as compared to anions, which are negatively charged ions) an element lower in the series (more positive) will deposit first, and an element higher in the series (more negative) will deposit only when the solution is practically depleted of the ions of the first element. Also called "electrochemical series" and "galvanic series."

An "element" is a substance that cannot be decomposed into simpler substances by chemical means.

The term "oxidation" means losing electron to oxidize. The term "reduction" means gaining electrons to reduce. The term "redox reaction" refers to any chemical reaction which involves oxidation and reduction. All electron-transfer reactions, i.e., chemical reaction where an electrical charge (usually an electron) is transferred from one reactant to another, are considered oxidation/reduction. The substance gaining electrons ("oxidizing agent" or "oxidant") is oxidizing the substance that is losing electrons ("reducing agent" or "reductant"). In the process, the "oxidizing agent" is itself reduced by the "reducing agent." Consequently, the reduction process is sometimes called "electronation," and the oxidation process is called "de-electronation."

The "standard electrode potential" is equilibrium potential (i.e., the electrical potential of an electrode measured against a reference electrode when there is no current flowing through the electrode) of an electrode when both the oxidized and the reduced species are present in unit concentration (strictly speaking, "activity") in the solution; if the "reduced" form is a metal, a pure metal (not alloyed with other metals) is considered to be at unit concentration. The standard potentials are always expressed against the standard hydrogen electrode, the potential of which is substantially zero. Standard potentials are a function of the temperature, and are usually tabulated for 25° C. Standard potentials are also called "normal electrode potential." The standard potential is the electromotive force of an electrochemical cell (i.e., a device that converts chemical energy into electrical energy or vice versa when a chemical reaction is occurring in the cell) comprised of the electrode in question and the standard hydrogen electrode. Strictly speaking, one must use unit activities rather than concentrations.

An "electrode" an electronically conducting part of an electrochemical cell. It can be an anode or a cathode. It can be a simple metallic structure (rods, sheets, etc) or much more complicated, composite structures.

The term "polarization" refers to a change of potential of an electrode from its equilibrium potential upon the application of a current.

The term "total acid number" (or "neutralization number" or "acid value" or "acidity") or TAN is a measure of both the weak organic and strong inorganic acids present within a sample such as lube oil. TAN is the mass of potassium hydroxide (KOH) in milligrams that is required to neutralize one gram of a sample such as lube oil. TAN is a measure of the amount of carboxylic acid groups in a chemical compound such as lube oil. In a typical procedure, a known amount of sample dissolved in organic solvent is titrated with a solution of potassium hydroxide with known concentration and with phenolphthalein as a color indicator.

High operating temperatures severely stress the oil. This results in oxidation and nitration, changes in viscosity, the build up of acidic waste products and deposits on metal surfaces. Testing for TAN is desired to maintain and protect your equipment, preventing damage in advance. A rise in TAN is indicative of oil oxidation due to time and/or operating temperature. Trend as well as absolute values should be used to monitor TAN levels. There are standard methods for determining the acid number, such as ASTM D 974 and DIN 51558 (for mineral oils, biodiesel).

The term "total base number" or TBN of oil is the measure of the alkaline reserve, or the ability of the oil to neutralize acids from combustion. TBN is measured by the quantity of acid, expressed in terms of the equivalent number of milligrams of potassium hydroxide that is required to neutralize all basic constituents present in 1 gram of a sample such as lube oil. (ASTM Designation D 974.) Severe depletion of the TBN results in acid corrosion and fouling within the engine. Maintaining a correct alkaline reserve prevents unnecessary corrosion of the upper piston, piston rings and top end bearing. Additionally, low TBN is indicative of reduced oil detergency. Low TBN could cause corrosion of combustion space and bearings and fouling within the engine.

TBN determines how effective the control of acids formed would be during the combustion process. The higher the TBN, the more effective it is in suspending wear-causing contaminants and reducing the corrosive effects of acids over an extended period of time. The associated measurement ASTM D2896 and ASTM D4739-06 generally range from 6-80 mg KOH/g in modern lubricants, 7-10 mg for general automotive use and 10-15 for Diesel operations. Marine grade lubricants generally will run from 15-50 mgKOH/g, but can be as high as 70 or 80 mg KOH/g as is the case of Exxon's MobileGuard 570 or respectively Castrol's Cyltech 80AW this high level is designed to allow a longer operating period between changes, under harsh operating conditions. When the TBN is measured at 2 mg KOH/g or less the lubricant is considered inadequate for engine protection, and is at risk for allowing corrosion to take place. Higher sulphur fuel will decrease the TBN faster due to the increased formation of sulphuric acid.

It is a widely held belief that the TBN (also called Base Number) of oil is required to prevent acidic corrosion within the combustion chamber of a running engine. This implies that it protects the piston rings, cylinder liner and piston crown from damage by sulphur or nitrogen containing acids.

Oils within an engine tend to deteriorate due to reasons of temperature, fuel ingress or other sources of contaminants forming harmful deposits. These deposits can build up behind piston rings, on ring lands, under the piston crown or on sliding surfaces. The net result is sticking and increased wear. Lubricating oils contain detergents and dispersants to delay the formation of these deposits and reduce the rate at which they form. Detergents are generally considered as those compounds that neutralize the deposit precursors that form under high temperature and pressure conditions or as the results of using high sulphur fuel. Dispersants on the other hand are those compounds that disperse or suspend the deposit forming contaminants.

The principal detergents are soaps and salts of alkaline metals, usually calcium in the case of marine oils; they are often referred to as metallo-organic compounds such as sulphates, phenates and salicylates. These compounds are usually "over based". They contain more alkaline metal than is required to neutralize the acidic components used in manufacture of the additive. These are usually ash forming and spent additive will contribute to the insolubles loading in a used oil.

Typical dispersants are usually "ash less". They do not form ash on combustion. Such dispersants include, for example, polymeric succinimides, polyesters and benzylamides. The molecules have a polar or charged end that will attract and hold on to potential deposit forming compounds keeping them in suspension in the oil.

The TBN additive could neutralize acidic combustion products. They could also neutralize deposit forming compounds within the oil, hold them in suspension preventing deposition and with luck also remove any deposits that are formed.

The embodiments of the invention relate to an oil management system (OMS) system to develop an on-line wireless oil (lubricant) quality monitoring systems for engine applications and, secondarily, other oil related applications. One of the tasks of automotive engine oil (lube oil) is the reduction of friction and wear, the provision of cooling and the suspension of contaminants. Engine oil commonly consists of a base stock of petroleum origin, combined with additives enhancing certain properties of the oil.

The base stock can be mineral base oils (refined petroleum crude oil) or synthetic oils. To this base stock up to 20% additives could be added in order to improve various properties of the final engine oil. Examples of such additives are anti-wear additives, viscosity modifiers (controlling the temperature dependence of the oil viscosity) antioxidants, detergents and antirust additives.

During service, oils continue to degrade until they no longer function as lubricants, and need to be replaced by fresh oils in order to protect the engine. Typically, the degradation of a lubricant can be considered to take place in four stages. Stage 1 denotes the depletion of detergents. For oil conductivity, this translates into a gradual drop (oil type A), or a rapid decrease (oil type B), which is caused by the consumption of electrically active compounds forming a part of the additive package. The amount of active compounds in fresh oil is dependent on the chemical composition of the detergents used. In Stage 2, the change in oil conductivity is minimal, signifying the completion of detergent depletion, and the onset of depletion of antioxidant. Stage 3 of the aging cycle begins with an increase in acidity (TAN), along with an increase in viscosity. Because of the conductive nature of acidic compounds, the oil conductivity increases throughout Stage 3. Published literature indicates that during this cycle of degradation, acidic compounds of acetates, formates, sulfates, and nitrates are formed. Completion of Stage 3 is characterized by the leveling off of the oil conductivity trend. In Stage 4, the oil conductivity starts to decline, primarily due to the increase in viscosity, which leads to lower ionic mobility. Acidity also continues to increase but tends to be dominated by the increase in viscosity.

| Stages of degradation | Detergent, related compounds | Antioxidant, related compounds | TAN | Viscosity | Sensor output |
|---|---|---|---|---|---|
| Stage 1 | Begins to inactivate | No change | No change | No change | Various |
| Stage 2 | Complete inactivation | Begins to inactivate | Gradual increase | No change | Steady |
| Stage 3 | — | Complete inactivation | Increase | Increase | Gradual increase |
| Stage 4 | — | — | Continued increase | Increase | Gradual decrease |

To evaluate the deterioration of engine oil during usage, a number of laboratory tests on used oil samples can be performed such as TAN (measuring acidity) and TBN (measuring alkalinity), flash point, contamination (by water, glycol, fuel), remaining additive concentration and viscosity, etc. Among these the most important parameters will be discussed below.

First, chemical oil deterioration due to oxidation is associated with an increase in viscosity whereas mechanical wear (cracking of organic chain molecules) and fuel dilution lead to decrease in viscosity. For diesel vehicles, the first factor increases continuously dominating the second factor. The viscosity has a strong temperature dependence which has to be accounted for when implementing a viscosity sensor for a large temperature range.

Secondly, acidity is one of the most important oil degrading parameters to be monitored and controlled in the automotive engine oil. The acidity of lube oil increases due to several factors: (1) degradation of lubricant additives such as antioxidants and detergents; (2) lubricant base oil degradation due to oxidation of hydrocarbons, (3) nitration of nitrogen-containing compounds, and sulphonation of sulfur-containing compounds; and (4) other contamination such as water contamination.

Finally, since no solid surface is perfectly smooth, opposing friction surfaces have peaks called asperities that come in contact with each other. As is known, rubbing of metal engine parts inevitably produces some microscopic metallic particles from the wearing of the surfaces. Such particles could circulate in the oil and grind against the part surfaces causing erosion and wear.

In summary, lube oil has three components that could be monitored:
Oil Additives
Anti-oxidants to prevent the breaking down of base oils and/or other oil additives due to oxidation
pH control (detergent) to neutralize acidic contaminants that corrode metal surfaces
Dispersant to keep particulates suspended.
The Base Oil Itself
Viscosity
Lubricity
Solids
Fine carbon particles ("soot"), important only for diesel
Large "agglomerated" carbon particles, important only for diesel
Metal particles, important for all engines
Some important measurements of a lube oil include:
1. pH (or possibly etch rate)
2. Viscosity
3. Particulates including metallic particles and carbon particulate matter (soot)
4. Oil oxidation onset time The embodiments of the invention include a sensor system having thin or thick films of metals and metal alloys and/or inorganic or organic compounds or metal foils to monitor and control the acidity of the lubricating oil used for automotive vehicles. The sensor element could be corrodible and upon deterioration of the oil, the sensor would corrode and the resistance of the sensor would start increasing. Meanwhile, due to the corrosion of the metal-containing sensor element, the metal or the compound ions would be released into the oil and neutralize the acidity fully or partially. The resistance of the sensor element would start increasing slowly during the initial periods of the corrosion while the acidity of the oil is being neutralized. Subsequently, as the acidity of the oil increases further, the corrosion of the sensor element increases and the resistance of the sensor would start increasing rapidly. At this point, the sensor would give an indication for an oil change.

The lube oil monitored by the sensor of the embodiments of this invention could have different formulations and greatly vary from one manufacturer to another. Generally, lube oil contains a number of additives like paraffin, synthetic or combinations. Additives ranging from 5% to 30% of a base oil and will be made up of antioxidants. The TAN (total acid number) and TBN (total base number) values of the oil could be measured externally to determine the oil quality. However, external determination of the TAN and TBN values is more expensive and also time consuming. The sensor system of the embodiments of the invention would be inside the lube oil tank and monitor the oil acidity in-situ to prevent the engine parts wear and tear and to increase the life of the vehicle.

Presently, the lube oil is changed after 20,000 miles of running the heavy duty vehicles and for passenger cars it is 3000 to 5000 miles. With the incorporation of the sensor of the embodiments of the invention, one need not change the oil by monitoring the miles; on the contrary, one can change the oil till the sensor reports the oil acidity to the predetermined value. This way, the oil change intervals can be monitored and unnecessary change of oil would save money as well as decrease the environmental pollution associated with an oil change, particularly resulting from the disposal of the used oil.

The sensor of the embodiments of the invention could be wireless such that the data from the sensor could be transmitted to a receiver without any wired connection. In addition, the embodiments of the sensor of the invention could have following features and/or abilities to determine the following properties: (1) engine wear and oil quality (2) oil viscosity; (3) oil conductivity; (4) lubricity; and (5) oil filter wear and quality.

As an illustrative example of the embodiments of the real-time corrosion sensor, the invention provides a sensor made of corrodible elements. In a preferred embodiment, the corrodible element may comprise a metal foil or wire of known dimensions wherein the metal foil or wire is chosen from the electrochemical activity series that is known to corrosion engineers. The series may be summarized as: K, Na, Ba, Mg, Al, Zn, Fe, Ni, Sn, Pb, Cu and Ag, etc. In another preferred embodiment, the corrodible element may comprise a metal alloy made of metals from the above list. In still another embodiment, the corrodible element may comprise metal oxides. The foils or wires could have a thickness/diameter in the range from about 1 nanometer to 1 mm, preferably in the range from about 5 microns to 0.5 mm, more preferably in the range from about 10 microns to 0.25 mm, and most preferably in the range from about 2 nanometers to 0.01 mm.

The electrochemical activity series and the interplay and distinction among its elemental members provide the necessary graduation and calibration of a lubricant response. The intensity of a lubricant is determined from real-time observation of corrosion on each of the test fuses. Depending upon the situation, the first metal foil or wire comprises K, the second comprises Na and so on.

The embodiments of the invention also relate to the corrosion sensor array comprising individual corrodible elements for measuring various elements and ions, such as chloride, sulfide, copper, hydrogen (pH), etc. and elements for evaluating the instantaneous corrosion properties of structural materials. The exact combination and number of elements measured or monitored could depend upon the environmental conditions and materials used which are subject to corrosive effects. Such a corrosion monitoring system embedded in or mounted on a structure exposed to the environment could serve as an early warning system for the onset of severe corrosion problems for the structure, thus providing a safety factor as well as economic factors in various applications, e.g., engine maintenance.

The embodiments of the invention also relate to the corrosion sensors and/or sensor arrays that can be connected to an electronics/computational system, which could provide a means for data collection and analysis. In process of measurement, the corrosion sensor is exposed to the lubricant for a fixed duration (thin metal foil or wires for short tests, thicker metal foil or wires for longer tests) and the rate at which the metal foil or wires could be etched or oxidized by the surroundings could be determined from different approaches. In one preferred approach, the rate at which of the metal foil or wires could be etched or oxidized by the surroundings can be determined by light microscopy (or a magnifier viewing window against an enlarged graph paper background, or a reflectance beam to penetrate the smooth surface oxide layers e.g. aluminum). In a more preferred alternative approach, the rate at which the metal foil or wires could be etched or oxidized by the surrounding can be determined by measuring the impedance of the corrodible elements, i.e., by electrochemical impedance spectroscopy (EIS). In most measurements, the test series can begin from zinc onwards and truncate at say, thin gold (or gold alloy).

EIS uses very small excitation voltages, generally in the range of 5 to 10 mV peak-to-peak, through the corrodible element which forms an electrochemical cell. The current induced by this voltage could be measured and an impedance determined as a function of frequency. EIS is based on the fact that the behavior of an electrochemical cell and that of an electronic circuit are analogous. This allows equivalent circuit modeling of a given electrochemical cell. Fundamental AC circuit theory can then be applied to the circuit model and the results accurately correlated to reveal physical and chemical properties of the electrochemical cell. In the electrochemical cell having the corrodible element, the presence of a lubricant surrounding the corrodible element act to change the impedance of the corrodible element, which can be modeled as a resistor, a capacitor, an inductor or a combination of elements.

Performing EIS on a corrodible element involves applying ac voltage of varying frequencies through the corrodible element which could be immersed in a lubricant such as a conductive electrolyte. The current or impedance (magnitude and phase) could be measured between the two ends of the corrodible element. Prior to exposure of the corrodible elements to a lubricant, the corrodible elements could be maintained in their pristine state by storing them in a small vacuum airlock chamber where metal degradation could be substantially zero. During corrosion testing, the corrodible elements could be exposed to the lubricant. The corrosion sensor can be left open to suit dynamic measurement or kept sealed to demonstrate data offsite. In either case, a sample of the lubricant could be let into the corrosion sensor containing the corrodible elements using an assembly arrangement that provides substantially the same temperature and substantially the same pressure inside the corrosion sensor as that existing outside the corrosion sensor.

As an illustrative example, the procedures of using the corrosion sensor in this invention for oil quality measurement are as follows. Prior to exposure of the corrodible elements to a lubricant, the corrodible elements can be maintained in their pristine state by storing them in a small vacuum airlock chamber where metal degradation could be substantially zero. During corrosion testing, the small vacuum airlock chamber is opened and the corrodible elements are exposed to the lubricant. The corrosion sensor is then left open to suit dynamic measurement or kept sealed to demonstrate data offsite. In either case, a sample of the lubricant is brought into contact with the corrosion sensor containing the corrodible elements using an assembly arrangement that provides substantially the same temperature and substantially the same pressure inside the corrosion sensor as that existing outside the corrosion sensor.

As the corrosion sensor could be filled with the sample of the lubricant, the corrodible element would undergo a rapid polarization change from levels near that when there is substantially zero corrosion of the corrodible element to values approaching the maximum potential under the lubricant. The polarization change values of the corrodible element indicate whether minimal or no deterioration of the corrodible element has occurred, whether little or more corrosion damage can proceed, and whether the lubricant requires oversight and maintenance.

Besides those mentioned previously, the embodiments of the invention also have other advantages. First, since the thermal expansion coefficient of each material could be known and also the test temperature, an algorithm correlating the change in dimensions at higher temperature and etching rates can be developed. The sensitivity can be very high and can be used to quantify corrosion differences, for example, from one sea water having 27000 ppm of chlorides to another sea water having 35000 ppm of chlorides, by varying the measurement times. For greater sensitivity, higher surface area disks may be used instead of metal foil or wires. The stage can be motorized to simulate turbulence and wind flow over the corrodible element. Secondly, the corrosion sensor of the embodiments of this invention could be conformable sensors that could conform according to the shape of an object such as an oil filter or a lube oil tank. Finally, the sensors are capable of either multiple time applications or one-time applications. For highest accuracy and sensitivity, the corrosion sensor of the embodiments of the invention generally has one-time use capabilities.

The embodiments of the corrosion sensor of this invention are thus capable, of determining corrosion in real-time (i.e., as it occurs) and can initiate remedial measures when corrosion activity exceeds a critical threshold. The corrosion sensor could be capable of identifying the "maximum extent of corrosion" recorded. In addition, the corrosion sensor could have smart sensing capabilities that can be integrated and modified to suit particular environments and situations.

The corrosion sensor could comprise a vacuum airlock chamber or a small hermetically sealed non-metallic enclosure comprising a reference corrodible element, wherein corrosion of the reference corrodible element is substantially zero and is provided for automatic temperature compensation of the corrodible element by neutralizing a change of resistance of the corrodible element that occurs due to variations that impact both the corrodible element and the reference corrodible element. A Wheatstone bridge could be employed to do the automatic temperature compensation. A Wheatstone bridge is a well known technique.

In other embodiments, the smart corrosion sensing service can be designed to take remedial action such as introducing a dose of stimulus neutralizing additives, or display the need for remedial action.

Examples

Several lubricants and hydraulic oils were monitored using a corrosion sensor of the embodiment of this invention as shown in FIG. 1, which includes the following: an oil bath (1) containing a corrosion sensor and reference sensor (3) having metal plates, metal foils or wires or metal oxide plates, metal oxide films, or metal oxide wires (5); power supply (7); potentiometer (9); a circuit (11); a microprocessor (13) interfaced to the circuit (11) via either a wired or wireless connection (15) and interfaced to an alarm display (19) via either a wired or wireless connection (17).

Figure 2:
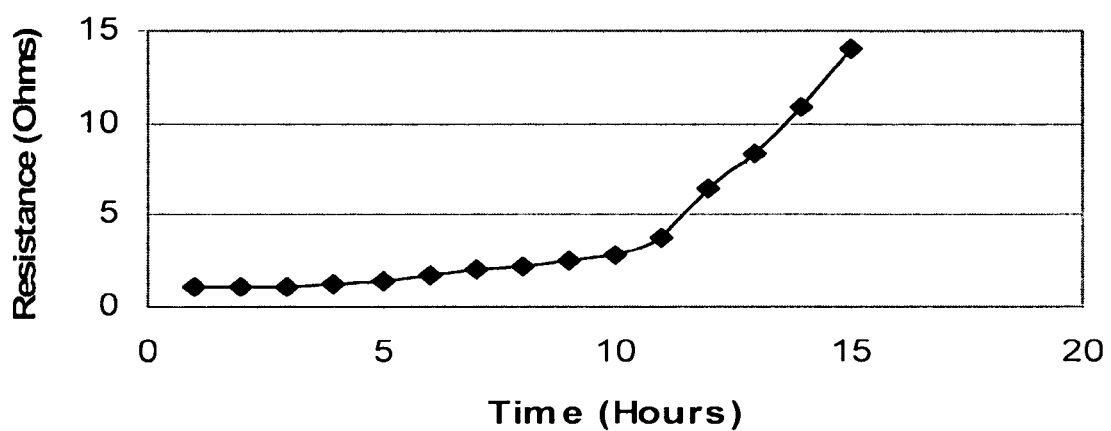
FIG. 2 shows the results of copper corrosion at 60° C. as a function of time in engine oil used for 30,000 kilometers.
Figure 3:
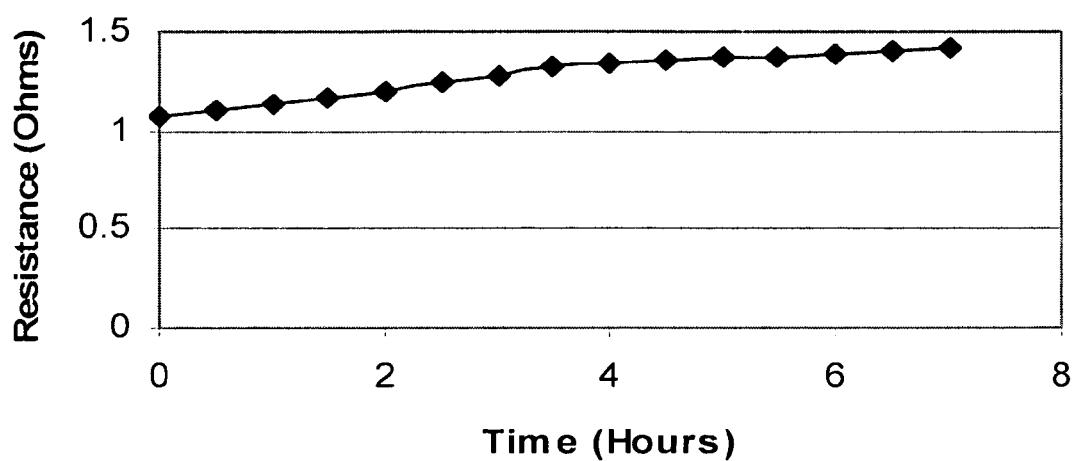
FIG. 3 shows the results of copper corrosion at 60° C. as a function of time in engine oil used for 20,000 kilometers.
Figure 4:
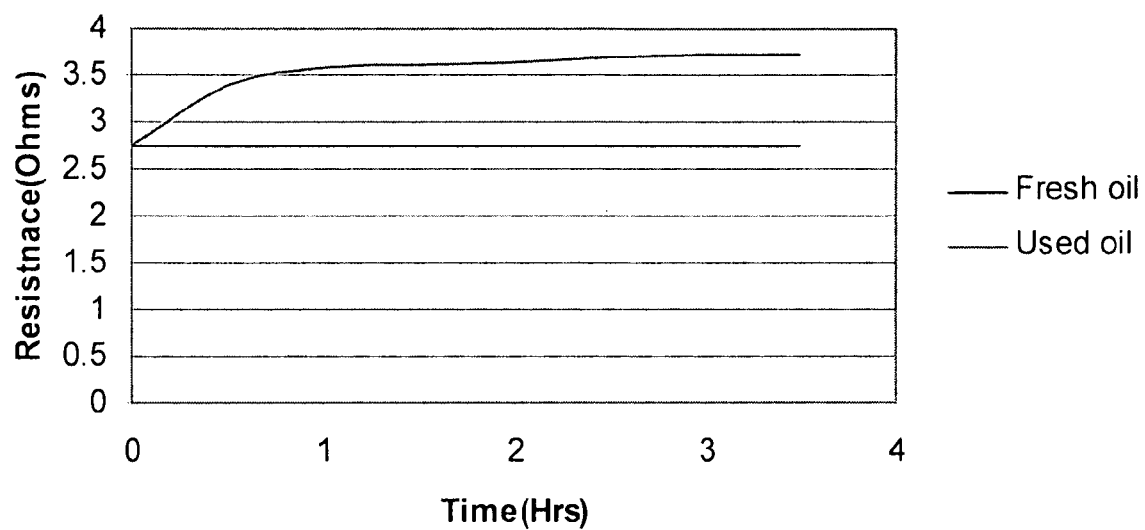
FIG. 4 shows the results of copper resistance change as a function of time in used and fresh lubricants at 60° C.

The results of the monitoring and controlling the pH of the lubricant in accordance with the experiment of FIG. 1 are shown in FIGS. 2-4. FIG. 2, entitled "Copper corrosion experiment at 60 degrees Centigrade for 30,000 KMs used engine oil" shows that the sensor resistance increases rapidly after an initial period of sensor corrosion and neutralization of the acidity of the used engine oil. FIG. 3, entitled "Copper corrosion experiment at 60 degrees Centigrade (° C.) for 20,000 KMs used engine oil" shows that the sensor resistance increases only slightly as the corrosion of the sensor is sufficient to neutralize the acidity of the used engine oil. FIG. 4 entitled "Copper resistance change in used [and fresh] lube oil at 50 (° C.) shows that sensor resistance increases slightly in used oil in which the sensor corrodes, while the sensor resistance does not increase in the fresh oil in which the sensor does not corrode.

Table 1 shows the data of atomic absorption spectroscopy for the fresh and used oils. The term "fresh oil" refers to lube oil as obtained from the manufacturer and the term "used oil" refers to lube oil collected from the trucks after running the trucks for 20 or 30 thousand kilometers. The fresh oil did not show any corrosion or degradation of the fresh oil by the corrosion sensor of the embodiments of the invention even the fresh oil was subjected to similar heating and testing conditions as that subjected to the used oil, which showed considerable change in the resistance of the sensor elements.

TABLE 1

Corrosion sensor test results of fresh and used oils

| | | Fresh Oil | | Used Oil | |
|---|---|---|---|---|---|
| | | Before Corrosion Sensor Testing | After Corrosion Sensor Testing | Before Corrosion Sensor Testing | After Corrosion Sensor Testing |
| TAN (mg KOH/gm) | Bangalore_Oil | 1.92 | 1.92 | 2.41 | 0.3 |
| | Sanghai_Oil | 1.03 | 1.03 | 2.9 | 0.5 |

TABLE 1-continued

Corrosion sensor test results of fresh and used oils

| | | Fresh Oil | | Used Oil | |
|---|---|---|---|---|---|
| | | Before Corrosion Sensor Testing | After Corrosion Sensor Testing | Before Corrosion Sensor Testing | After Corrosion Sensor Testing |
| TBN (mg KOH/gm) | Bangalore_Oil | 10.27 | 10.27 | 5.98 | 6.4 |
| | Sanghai_Oil | 8.1 | 8.1 | 3.4 | 3.4 |
| Copper Content (mg/Kg) | Bangalore_Oil | 0 | 0 | 3 | 13.6 |
| | Sanghai_Oil | 0 | 0 | 3 | 7.5 |

Table 1 clearly suggests that the used oil contains more copper after the corrosion sensor testing than before such testing. For similar corrosion sensor testing, the fresh oil did not show any copper addition. This clearly shows that the copper metal is corroded from the copper-containing sensor by dissolving into the used oil due to the acidity of the used oil.

While only certain features of the invention have been illustrated and described herein, many modifications and changes will occur to those skilled in the art. It is, therefore, to be understood that the appended claims are intended to cover all such modifications and changes as fall within the true spirit of the invention.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. An apparatus comprising:
    a corrosion sensor comprising a metal-containing corrodible element which is corrodible in a lubricant having an acidity level, wherein the acidity level is a measure of lubricant degradation and the corrosion sensor is configured to measure lubricant degradation in real time, wherein, in response to increasing corrosion, the metal-containing corrodible element is configured to release metal ions into the lubricant to control the acidity level, further wherein the increasing corrosion is associated with increasing resistance of the metal-containing corrodible element, wherein the corrosion sensor further comprises a reference corrodible element having a corrosion level of substantially zero; and
    an output device coupled to the corrosion sensor to display information related to the acidity level, the information based on the increasing resistance of the metal-containing corrodible element.

2. The apparatus of claim 1, wherein the metal-containing corrodible element comprises a metal plate, metal foil, a metal wire, or a metal oxide film.

3. The apparatus of claim 2, wherein the metal plate, metal foil, metal wire, or metal oxide film comprises an element selected from K, Na, Ba, Mg, Al, Zn, Fe, Ni, Sn, Pb, Cu, Ag and combinations thereof.

4. The apparatus of claim 2, wherein the metal is a metal alloy and the wire has a thickness and diameter in a range of about 1 nm to about 1 mm.

5. The apparatus of claim 1, wherein the reference corrodible element is located in a vacuum airlock chamber or a small hermetically sealed non-metallic enclosure.

6. The apparatus of claim 1 wherein the corrosion sensor is located in an engine containing the lubricant.

7. The apparatus of claim 6 wherein the engine is located in a vehicle and the information includes a recommendation to replace the lubricant.

8. The apparatus of claim 1 wherein the corrosion sensor is a one-time use corrosion sensor.

9. The apparatus of claim 1 wherein the corrosion sensor is a conformable corrosion sensor.

10. A system comprising:
- a corrosion sensor comprising a metal-containing corrodible element which is corrodible in a lubricant having an acidity level, wherein the acidity level is a measure of lubricant degradation and the corrosion sensor is configured to measure lubricant degradation in real time, wherein, in response to increasing corrosion, the metal-containing corrodible element is configured to release metal ions into the lubricant to control the acidity level, further wherein the increasing corrosion is associated with increasing resistance of the metal-containing corrodible element, wherein the corrosion sensor further comprises a reference corrodible element having a corrosion level of substantially zero;
- an electronic module connected to the corrosion sensor for receiving and analyzing data from the corrosion sensor, including data about the acidity level; and
- an output device coupled to the electronic module to display information related to the acidity level, the information based on the increasing resistance of the metal-containing corrodible element.

11. The system of claim 10, wherein the corrosion sensor is located in an engine containing the lubricant.

12. The system of claim 10, wherein the metal-containing corrodible element comprises a metal plate, metal foil, a metal wire, or a metal oxide film.

13. The system of claim 12, wherein the metal plate, metal foil, metal wire, or metal oxide film comprises an element selected from K, Na, Ba, Mg, Al, Zn, Fe, Ni, Sn, Pb, Cu, Ag and combinations thereof.

14. The system of claim 10, wherein the corrodible element comprises Cu.

15. The system of claim 10, wherein the reference corrodible element is located in a vacuum airlock chamber or a small hermetically sealed non-metallic enclosure.

16. The system of claim 15, further comprising wherein the reference corrodible element provides automatic temperature compensation of the metal-containing corrodible element.

17. The system of claim 10, wherein the reference corrodible element is a sealed reference corrodible element located in a hermetically sealed non-metallic enclosure, and the electronic module is capable of comparing an amount of corrosion of the metal-containing corrodible element with respect to the sealed corrodible element.

18. The system of claim 10 wherein the corrosion sensor is located in an engine containing the lubricant.

19. The system of claim 18 wherein the engine is located in a vehicle.

20. The system of claim 10 wherein the acidity level is a maximum acidity level.

21. A method comprising:
- with a corrosion sensor having a metal-containing corrodible element, sensing data pertaining to acidity of a lubricant, wherein the acidity level is a measure of lubricant degradation and the corrosion sensor is configured to measure lubricant degradation in real time;
- allowing the corrodible element to corrode, wherein, in response to increasing corrosion, the metal-containing corrodible element releases metal ions into the lubricant to control the acidity level, wherein the increasing corrosion is associated with increasing resistance of the metal-containing corrodible element;
- comparing an amount of corrosion with a reference corrodible element in communication with the corrosion sensor and having a corrosion level of substantially zero;
- determining an acidity level with the corrosion sensor; and
- providing acidity level data sensed by the corrosion sensor to an electronic module, the data based on the increasing resistance of the metal-containing corrodible element.

22. The method of claim 21, further comprising determining a rate at which the corrodible element is corroded.

23. The method of claim 22, wherein the step is performed by applying a voltage difference between two locations of the corrodible element.

24. The method of claim 22, wherein the determining step comprises measuring a potential which corresponds to a polarization of the corrodible element and measuring a current flowing through the corrodible element, wherein the polarization and the measured current output together indicate an amount of corrosion of the corrodible element.

25. The method of claim 22, wherein the reference corrodible element is a sealed reference corrodible element which located in a hermetically sealed non-metallic enclosure, wherein corrosion of the reference corrodible element is substantially zero.

26. The method of claim 22, wherein the determining step is performed by optical microscopy.

27. The method of claim 21, wherein the determining step is performed by electrochemical impedance spectroscopy.

28. The method of claim 21 wherein the acidity level is a maximum acidity level.

29. The method of claim 21 wherein the metal-containing corrodible element undergoes a polarization change from a level near substantially zero corrosion to values approaching a maximum potential.

* * * * *

UNITED STATES PATENT AND TRADEMARK OFFICE
CERTIFICATE OF CORRECTION

| | | |
|---|---|---|
| PATENT NO. | : 8,149,004 B2 | Page 1 of 1 |
| APPLICATION NO. | : 11/655271 | |
| DATED | : April 3, 2012 | |
| INVENTOR(S) | : Raghurama A. Raju et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 640 days.

Signed and Sealed this
Fifth Day of June, 2012

David J. Kappos
*Director of the United States Patent and Trademark Office*